United States Patent [19]

Gupta et al.

[11] Patent Number: 5,175,349
[45] Date of Patent: Dec. 29, 1992

[54] STABILIZATION OF ORGANIC POLYISOCYANATES

[75] Inventors: Pramod Gupta, Bedburg; Christian König, Kaarst; Hans-Jürgen Rabe, Leverkusen; Hans-Wilhelm Engels, Kerpen; Wilfried Nolte, Odenthal; Chiraranjan Podder, Dormagen, all of Fed. Rep. of Germany

[73] Assignee: Bayer Aktiengesellschaft, Leverkusen, Fed. Rep. of Germany

[21] Appl. No.: 663,212

[22] Filed: Mar. 1, 1991

[30] Foreign Application Priority Data

Mar. 7, 1990 [DE] Fed. Rep. of Germany ....... 4007074
Dec. 22, 1990 [DE] Fed. Rep. of Germany ....... 4041516

[51] Int. Cl.⁵ ............................................ C07C 263/18
[52] U.S. Cl. .................. 560/333; 252/182.2; 252/404; 524/291; 562/471
[58] Field of Search ............. 560/333; 252/404, 182.2

[56] References Cited

U.S. PATENT DOCUMENTS

| | | | |
|---|---|---|---|
| 3,281,444 | 10/1966 | Manning | 560/333 |
| 3,494,952 | 2/1970 | Nakata et al. | 560/330 |
| 3,678,047 | 7/1972 | Kletecka et al. | 560/330 |
| 3,715,381 | 2/1973 | Spaunburgh et al. | 560/330 |
| 3,723,489 | 3/1973 | Dexter et al. | 252/300 X |
| 4,064,157 | 12/1977 | Nafziger et al. | 560/330 |
| 5,068,402 | 11/1991 | Pedain et al. | 560/331 |

FOREIGN PATENT DOCUMENTS 1197437 7/1970 United Kingdom .

*Primary Examiner*—José G. Dees
*Assistant Examiner*—Vera C. Clarke
*Attorney, Agent, or Firm*—Joseph C. Gil; Godfried R. Akorli

[57] ABSTRACT

The present invention relates to the use of nucleus-substituted 4-hydroxyphenyl propionic acid compounds for stabilizing organic polyisocyanates.

1 Claim, No Drawings

STABILIZATION OF ORGANIC POLYISOCYANATES

This invention relates to the use of nucleus-substituted 4-hydroxyphenyl propionic acid compounds for stabilizing organic polyisocyanates.

Organic isocyanates have acquired considerable importance in the manufacture of polyurethane plastics. For example, organic polyisocyanates are used with polyols (polyethers and polyesters) for the manufacture of foams, fibers, films, elastomers and paints.

However, organic polyisocyanates tend to discolor in storage, even at low temperatures. This property is particularly pronounced when the organic polyisocyanates have to be stored at relatively high temperatures, for example when the solid polyisocyanates are to be homogeneously reacted with such reactants as, for example, polyether polyols, polyester polyols or glycols to form polyurethanes. In the production of polymers, the NCO-OH reaction also has to be carried out at relatively high temperatures. In this case, it has been found that the isocyanates discolor very quickly unless they have been stabilized.

It has already been proposed to add various stabilizers to organic isocyanates to reduce their tendency towards discoloration. Known stabilizers include sterically hindered phenols, dialkyl diphenyl amines, phenothiazines, phosphites and mixtures of representatives of these classes of compounds (cf. for example U.S. Pat. No. 3,715,381, U.S. Pat. No. 4,064,157, DT-OS 1 668 275, DT-AS 1 618 845).

2,6-Di-tert. butyl-4-methyl phenol (BHT) either on its own or in combination with other compounds from the classes mentioned is the most widely used stabilizer for organic polyisocyanates.

Disadvantages of BHT include its relatively high volatility and its tendency to migrate into substrates surrounding polyurethanes and also the resulting pronouced yellowing of the substrates in NOx-contaminated atmospheres. Stabilizers without these disadvantages would be of interest and the problem addressed by the present invention was to provide such materials.

Metal salts of 3,5-di-tert. butyl-4-hydroxyphenyl propionic acid are described in DE-OS 2 209 102 for the stabilization of organic material, their substrate-dependent activity being critically determined by the metal atom used.

The present invention relates to the use of compounds corresponding to the following general formula

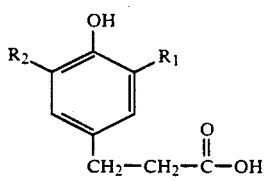

in which

R$_1$ and R$_2$ may be the same or different and represent C$_{1-8}$ alkyl radicals, preferably C$_{1-4}$ alkyl radicals, as stabilizers for organic polyisocyanates, more particularly aromatic polyisocyanates.

Although free carboxyl groups as substituents do not normally lead to particularly effective stabilizers so that derivatives of carboxylic acids, such as esters, amides, hydrazides, etc., are generally used, it has now surprisingly been found that compounds belonging to the class of nucleus-substituted 4-hydroxyphenyl propionic acids, such as 3,5-di-tert. butyl-4-hydroxyphenyl propionic acid for example, are eminently suitable as (stabilizing) antioxidants for organic polyisocyanates.

Depending on the basic structure of the polyisocyanate, combinations with conventional antioxidants are also effective. The compounds of this class (such as 3,5-ditert. butyl-4-hydroxyphenyl propionic acid) may be used in quantities of from 0.003 to 1.0% by weight and preferably in quantities of 0.003 to 0.5% by weight and, in the case of combination stabilizers, in quantities of 0.003 to 0.5% by weight, based on the polyisocyanate.

The nucleus-substituted 4-hydroxyphenyl propionic acid compounds, which are produced by base-catalyzed addition of methyl acrylate onto substituted phenols and subsequent saponification (cf. DE 2 120 285), are suitable for all the usual polyisocyanates, including aliphatic, aromatic and cycloaliphatic polyisocyanates. Examples of such polyisocyanates are ethylene diisocyanate, tetramethylene diisocyanate, hexamethylene diisocyanate, cyclohexyl diisocyanate, 4,4'-methylene-bis-(cyclohexylisocyanate), m-phenylene diisocyanate, p-phenylene diisocyanate, tolylene-2,4diisocyanate, tolylene-2,6-diisocyanate, 4,4'-methylene-bis-(phenylisocyanate), 2,2'-methylene-bis-(phenylisocyanate), 2,3-methylene-bis-(phenylisocyanate), tolylene-2,4,6-triisocyanate.

The organic polyisocyanates thus stabilized show a greatly reduced tendency to discolor during storage at elevated temperatures and may be used with advantage for the production of polyurethanes. The polyurethanes in turn are used for the manufacture of foams, films, paints and elastomers.

The invention is illustrated by the following Examples (percentages are by weight and all temperatures are in C) The APHA color value (CV) was determined in accordance with DIN 53 409 (July, 1967) or ISO (July, 1988).

EXAMPLES

Example 1

A mixture of 80% tolylene-2,4-diisocyanate and 20% tolylene-2,6-diisocyanate was mixed with the following quantities of additives:

|  | APHA color value after | | |
|---|---|---|---|
|  | 6 | 15 | 21 days |
| Desmodur ® T 80 (toluene diisocyanate; 2,4 80%; 2,6 20%) With no addition | 10 | 50 | 1000 |
| With addition of | | | |
| 30 ppm BHT[1)] | — | — | 250 |
| 100 ppm BHT | — | — | 150 |
| 30 ppm BHP[2)] | — | — | 150 |
| 100 ppm BHP | — | — | 150 |

The above figures show that the addition of 30 ppm BHP has a similar stabilizing effect to the addition of 100 ppm BHT.

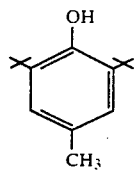

3,5-di-tert. butyl-4-hydroxy toluene

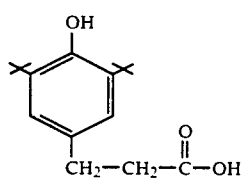

3,5-di-tert. butyl-4-hydroxyphenyl propionic acid

EXAMPLE 2

Diphenylmethyl methane diisocyanate (Desmodur(®) 44) (DPMMD) was mixed with the stabilizer according to the invention in the following quantities:

Sample A: 500 g DPMMD + 50 mg BHT[1]
Sample B: 500 g DPMMD + 50 mg BHT[2]
Sample C: DPMMD with no addition The samples were subjected to a UV irradiation test to determine yellowing. After 70 hours exposure, the samples had the following APHA color values:

|                    | APHA color value |
|--------------------|------------------|
| Sample A           | 100              |
| Sample B           | 60               |
| Sample C           | 250              |
| Before irradiation | 0 to 5           |

| | APHA color value |
|---|---|
| 1) 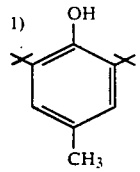 | 3,5-di-tert. butyl-4-hydroxy toluene |
| 2) (structure) | 3,5-di-tert. butyl-4-hydroxyphenyl propionic acid |

EXAMPLE 3

The same isocyanate as in Example 1 was mixed with the following additives:

| | APHA color value after | | | |
|---|---|---|---|---|
| | 3 | 7 | 12 | 18 days |
| With addition of | | | | |
| 30 ppm BHT[1] | — | — | 5 | 150 |
| 30 ppm DHP[2] | — | — | 5 | 150 |

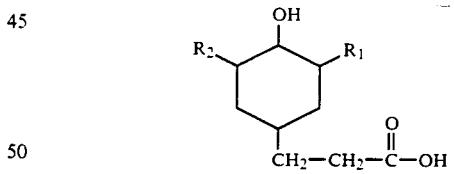

1) 3,5-di-tert. butyl-4-hydroxytoluene 2) 3,5-di-methyl-4-hydroxyphenyl propionic acid

We claim:
1. A process for stabilizing an organic polyisocyanate comprising adding to the polyisocyanate an effective amount of a compound corresponding to the following formula:

(structure shown)

in which
$R_1$ and $R_2$ are the same or different and represent a $C_1$ to $C_8$ alkyl radical.

* * * * *